United States Patent [19]

Bochis et al.

[11] 4,096,264

[45] Jun. 20, 1978

[54] CERTAIN SUBSTITUTED IMIDAZO [1,2,-a] PYRIDINES

[75] Inventors: Richard J. Bochis, East Brunswick; Peter Kulsa, Plainfield, both of N.J.

[73] Assignee: Merck & Co., Inc., Rahway, N.J.

[21] Appl. No.: 718,652

[22] Filed: Aug. 26, 1976

Related U.S. Application Data

[63] Continuation-in-part of Ser. No. 639,034, Dec. 9, 1975, abandoned.

[51] Int. Cl.$^2$ ............... A61K 31/44; C07D 401/02
[52] U.S. Cl. .................. 424/256; 260/294.8 F; 260/294.8 C; 260/294.9; 260/295 F
[58] Field of Search .............. 424/256; 260/294.8 C, 260/295 K, 296 B, 296 H, 295 F

[56] References Cited

U.S. PATENT DOCUMENTS

| | | | |
|---|---|---|---|
| 3,701,780 | 10/1972 | Fisher | 260/294.8 C |
| 3,790,586 | 2/1974 | Irikura et al. | 260/296 H |

OTHER PUBLICATIONS

Burger, Medicinal Chemistry, pp. 42–43, Interscience Publishers, NY (1960), 2nd ed.
Fisher et al., J. Med. Chem., vol. 15, pp. 982–985 (1972).

*Primary Examiner*—Alan L. Rotman
*Attorney, Agent, or Firm*—David L. Rose; J. Jerome Behan

[57] ABSTRACT

Certain novel substituted imidazo [1,2-a] pyridines with a substituted amino group at the 2- or 3-position are active anthelmintic agents. The novel compounds are prepared from the appropriate substituted 2-aminopyridine precursor. Compositions which utilize said novel imidazo [1,2-a] pyridines as the active ingredient thereof for the treatment of helminthiasis are also disclosed.

28 Claims, No Drawings

CERTAIN SUBSTITUTED IMIDAZO [1,2-a] PYRIDINES

CROSS-REFERENCE TO RELATED APPLICATIONS

This application is a continuation-in-part of my application Ser. No. 639,034, filed Dec. 9, 1975, now abandoned.

SUMMARY OF THE INVENTION

This invention is concerned with novel organic compounds which are classified as imidazo [1,2-a] pyridines which are variously substituted on the pyrido ring and at the 2- or 3- positions with a substituted amino group. Such compounds are active anthelmintic agents. Thus, it is an object of this invention to disclose novel substituted imidazo [1,2-a] pyridines which have anthelmintic activity.

It is a further object of this invention to disclose processes for the preparation of such compounds. A still further object of this invention is to disclose compositions containing such compounds as the active ingredient for the treatment of helminthiasis. Further objects will become apparent upon reading the following Description of the Invention.

DESCRIPTION OF THE INVENTION

The novel substituted imidazo [1,2-a] pyridines of this invention are best realized in the following structure:

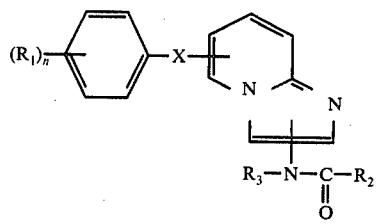

wherein

X is oxygen, sulfur, sulfinyl or sulfonyl;

$R_1$ is halogen, trifluoromethyl, loweralkyl, loweralkoxy, loweralkoxycarbonyl, loweralkylthio, loweralkylsulfinyl, loweralkylsulfonyl, loweralkanoyl, hydroxy, sulfonamido, mono- or di-loweralkylsulfonamido, amino, mono- or di-loweralkylamino, carboxy, carboxamido, mono- and di-loweralkylcarboxamido, loweralkanoyloxy, loweralkoxycarbonylamino, loweralkanoylamino, cyano or nitro;

$n$ is 0, 1 or 2 such that when $n$ is 2 the two $R_1$ groups need not be identical.

$R_2$ is loweralkyl or loweralkoxy; provided that when X is oxygen, $n$ is 1 or 2; and $R_3$ is hydrogen, loweralkyl, loweralkenyl, or loweralkyl substituted with loweralkoxy, loweralkoxycarbonyl, carboxy, loweralkylthio, loweralkylsulfinyl, loweralkylsulfonyl, amino and mono- or di-loweralkylamino, phenyl, halophenyl, or loweralkoxyphenyl.

In the instant application, the following numbering system is employed for the imidazo [1,2-a] pyridine ring system:

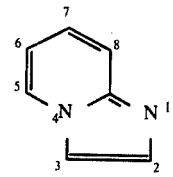

The term "loweralkyl" is intended to include those alkyl groups containing from 1 to 6 carbon atoms of either a straight or branched configuration such as methyl, ethyl, propyl, butyl, amyl, hexyl, isopropyl, tert butyl and the like.

The term "loweralkenyl" is intended to include those alkenyl groups which contain from 2 to 6 carbon atoms and one or two unsaturations such as vinyl, propenyl, butenyl, butadienyl and the like.

The term "loweralkoxy" is intended to include those alkoxy groups containing from 1 to 6 carbon atoms of either a straight or branched configuration such as methoxy, ethoxy, propoxy, butoxy, amyloxy, hexyloxy, isopropoxy, tert-butoxy, and the like.

The term "loweralkanoyl" is intended to include those alkanoyl groups of from 2 to 6 carbon atoms such as acetyl, propionyl, butyryl, and the like.

The term "halogen" is intended to include the halogen atoms fluorine, chlorine, bromine and iodine.

PREFERRED EMBODIMENTS OF THE INVENTION

One aspect of the preferred embodiments of this invention is realized when the amino group is in the 2-position and the phenyl containing substituent is in the 6-position of the imidazo [1,2-a] pyridine molecule.

Another preferred aspect of this invention is realized when $R_2$ is a loweralkoxy group, particularly methoxy or ethoxy, and $R_3$ is hydrogen or loweralkyl, particularly methyl or ethyl.

A still further preferred aspect of this invention is realized when $n$ is 0 or 1. It is preferred in the foregoing structural formula (I) to have X represent thio, sulfinyl, or sulfonyl and in particular the sulfinyl group.

When $n$ is 1 it is preferred that $R_1$ represent amino, loweralkanoylamino, loweralkoxy, loweralkylsulfinyl, mono- and diloweralkylamino, or loweralkyl, and that such groups are in the 3- or 4- positions of the phenyl ring.

Preferred from among the foregoing groups are the amino, loweralkanoylamino, and loweralkoxy groups in the 4-position of the phenyl ring.

Particularly preferred are those compounds wherein X is sulfinyl; $n$ is 0 or 1; $R_2$ is methoxy; $R_3$ is hydrogen; the substituted amino group is in the 2-position; and $R_1$ is amino, acetamido, or methoxy in the 4-position of the phenyl group which is in the 6-position of the imidazo [1,2-a] pyridine group.

The most preferred compound 2-(methoxycarbonylamino)-6-phenylsulfinyl-imidazo [1,2-a] pyridine.

Examples of other preferred compounds of this invention are:

2-(Methoxycarbonylamino) 6-(phenylthio)-imidazo [1,2-a] pyridine
2-(Ethoxycarbonylamino) 6-(phenylsulfonylimidazo) [1,2-a] pyridine
2-(Methoxycarbonylamino)-6-(3--acetamidophenylthio) imidazo [1,2-a] pyridine 2-(Methoxycarbonylamino)-6-(3-acetamidophenylsulfinyl) imidazo [1,2-a] pyridine
2-(Methoxycarbonylamino)-6-(3-acetamidophenylsulfonyl) imidazo [1,2-a] pyridine
2-(Methoxycarbonylamino)-6-(3-aminophenylthio) imidazo [1,2-a] pyridine
2-(Methoxycarbonylamino)-6-(3-aminophenylsulfinyl) imidazo [1,2-a] pyridine
2-(Methoxycarbonylamino)-6-(3-aminophenylsulfonyl) imidazo [1,2-a] pyridine
2-(Methoxycarbonylamino)-6-(3-methoxyphenylthio) imidazo [1,2-a] pyridine
2-(Methoxycarbonylamino)-6-(3-methoxyphenylsulfinyl) imidazo [1,2-a] pyridine
2-(Methoxycarbonylamino)-6-(3-methoxyphenylsulfonyl) imidazo [1,2-a] pyridine
2-(Methoxycarbonylamino)-6-(4-methylsulfinylphenylthio) imidazo [1,2-a] pyridine
2-(Methoxycarbonylamino)-6-(3-methylsulfinylphenylsulfinyl) imidazo [1,2-a] pyridine
2-(Methoxycarbonylamino-6-(4-aminophenylsulfinyl) imidazo [1,2-a] pyridine
2-(Methoxycarbonylamino)-6-[4-(N,N-dimethyl)-phenylsulfinyl] imidazo [1,2-a] pyridine
2-(Methoxycarbonylamino-6-(4-methylphenylsulfinyl) imidazo [1,2-a] pyridine
2-[Ethyl-N-(methoxycarbonyl)amino-6-(phenylthio)imidazo [1,2-a] pyridine
2-[Ethyl-N-(acethoxycarbonyl)amino]-6-(phenylsulfinyl) imidazo [1,2-a] pyridine
2-[Methyl-N-(methoxycarbonyl)amino]-6-(phenylthio) imidazo [1,2-a] pyridine
2[Methyl-N-(methoxycarbonyl)amino]-6-(phenylsulfinyl) imidazo [1,2-a] pyridine
2-(Methoxycarbonylamino) 6-(4-aminophenylthio) imidazo [1,2-a] pyridine
2-(Methoxycarbonylamino) 6-(4-aminophenylsulfonyl) imidazo [1,2-a] pyridine The compounds of this invention wherein the amido group is at the 2-position of the imidazo [1,2-a] pyridine molecule, are prepared by reacting an appropriately substituted 2-aminopyridine according to the following reaction scheme:

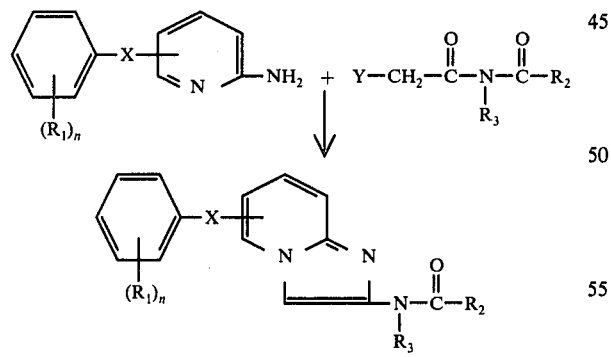

wherein X, $R_1$, $R_2$, $R_3$ and $n$ are as previously defined and Y is a halogen selected from chlorine, bromine and iodine. The reactants are combined in a solvent which for optimum results should be a polar aprotic solvent. Suitable solvents are: acetonitrile, dimethylformamide, hexamethylphosphoramide, dimethylacetamide, dimethoxyethane, and the like. The reaction may be conducted at from 50 to 150° C. over a period of from 1 to 50 hours, however, it is preferred to heat the reaction at from 75 to 100° C. for from 1 to 24 hours. The reaction product is isolated by techniques known to those skilled in this art.

Alternatively the compounds of this invention may be prepared by treating the metal salt of a protected 2-amino pyridine compound with a halo acetamide and treating the product with a cyclizing reagent such as trifluoroacetic anhydride, acetic anhydride or propionic anhydride.

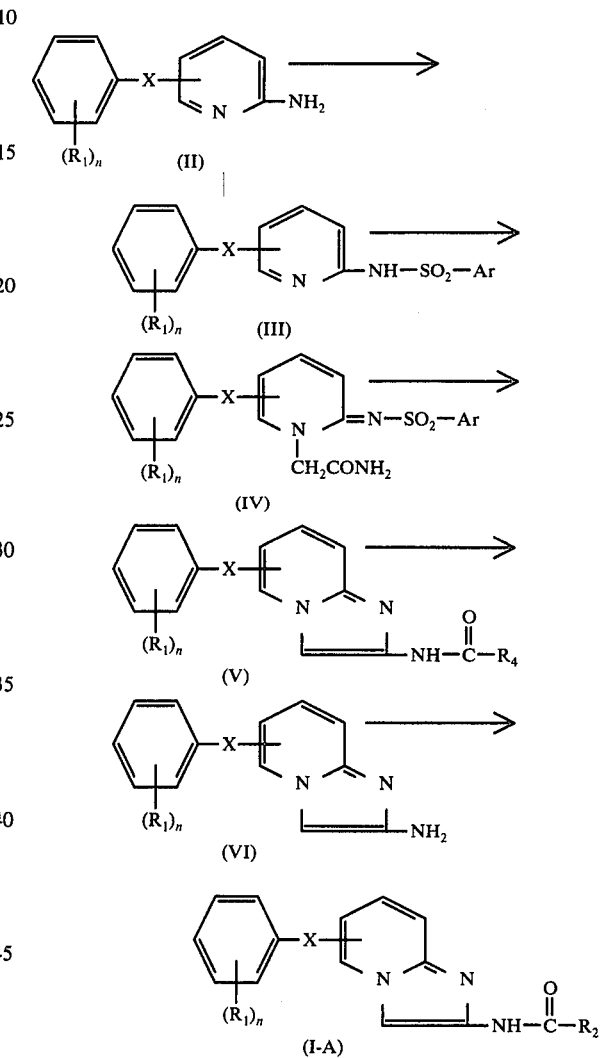

wherein X, $R_1$, $R_2$ and $n$ are as previously defined, Ar is an aryl protecting group and $R_4$ is loweralkyl or trifluoromethyl.

The 2-amino function of compound (II) is protected with an aryl sulfonyl group as indicated in the first step of this reaction. It is preferred to utilize the p-tolyl sulfonyl group which is prepared by treating compound (II) with p-tolyl sulfonyl chloride. Alternatively a suitably substituted 2-chloro pyridine could be treated with a metal salt of p-tolyl sulfonamide. The reaction with p-tolyl sulfonyl chloride is generally conducted in a basic solvent such as pyridine at from room temperature to 100° C for from ½ to 12 hours. The p-tolylsulfonamide reaction is generally conducted in a polar solvent such as dimethyl formamide at from 50 to 150° C for from 1 to 12 hours.

The protected compound (III) is then treated with a haloacetamide following the preparation of the corresponding metal salt. The metal salt, preferably the alkali metal salt, is prepared by treating the protected pyridine compound (III) with a metal hydride in a solvent such as dimethylformamide for from ½ to 6 hours at from room temperature to 100° C. The metal salt is then treated with a haloacetamide, preferably chloroacetamide. The reaction is run at from room temperature to 100° C for from ½ to 6 hours and the product (IV) isolated using techniques known to those skilled in this art.

The protected 1-acetamido-2-amino pyridine (IV) is cyclized by treatment with a suitable cyclization reagent. It is preferred to utilize trifluoroacetic anhydride, however, loweralkanoic anhydrides are also suitable. The anhydride is generally employed in great excess such that it also serves as a solvent. Thus, no separate solvent need be employed and the reaction is conducted at from room temperature to 100° C for from ½ to 6 hours. The reaction is generally complete, however, in from 1 to 3 hours at from 40° to 75° C.

The acetamido group of compound (V) is hydrolized to the amino group by treatment with aqueous base. Stirring at from room temperature to 50° C in an aqueous solution or suspension of an alkali metal hydroxide, carbonate or bicarbonate is generally sufficient to prepare the 2-amino compound (VI).

The 2-amino compound is readily converted to the 2-amido products of this invention (I-A) by acylation techniques. Acylating groups containing the function:

such as acyl halides, anhydrides, alkyl haloformates and the like are suitable. The reaction is generally complete in from 5 minutes to 2 hours at from room temperature to 50° C. In certain cases there is an initial exotherm which will necessitate the application of external cooling. In addition, where the reaction process liberates a hydrohalic acid such as when an acid halide or a haloformate is employed, it is advisable to include in the reaction mixture a single molar equivalent of a base. Inorganic and organic bases may be employed such as alkali metal carbonates or bicarbonates and tertiary amines such as pyridine and triethylamine. The products (I-A) are isolated using techniques known to those skilled in this art.

The compounds wherein $R_3$ is hydrogen (I-A) are readily converted to the compounds wherein $R_3$ is other than hydrogen by alkylation techniques.

Generally compounds I-A are converted to a metal salt, preferably an alkali metal salt such as lithium, sodium or potassium, by treatment with a base. Preferred bases are alkali metal hydrides or hydroxides, or butyl lithium diisopropylamide. The reaction is generally conducted in an inert solvent such as dimethylformamide, tetrahydrofuran, dimethylsulfoxide and the like, at from room temperature to the reflux temperature of the reaction mixture. Generally, however, a maximum temperature of about 100° C is sufficient. The reaction is generally complete in from 5 minutes to 2 hours.

The metal salt of compound I-A is then treated with the halide of an $R_3$ group in order to form the $R_3$ substituted compounds. The reaction is generally carried out in the same reaction vessel employed for the preparation of the metal salt. It is generally not necessary to isolate the metal salt, so that it then becomes desireable to add the $R_3$ halide directly to the metal salt reaction mixture. The reaction is generally complete in from 1 to 48 hours at from 0° to 100° C; however, it is preferred to carry out the reaction at room temperature. The products are isolated using techniques known to those skilled in this art.

Many of the 2-amino pyridine compounds which are starting materials for both of the foregoing processes are known in the chemical literature. Such compound, both those known in the art and those not heretofor described, may be prepared according to the following reaction scheme:

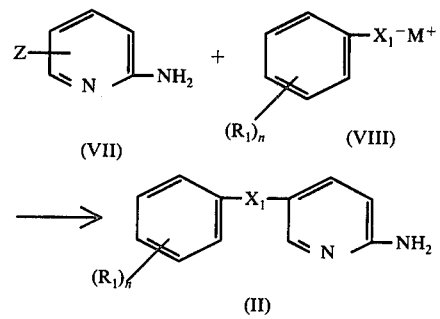

wherein $R_1$ and $n$ are as previously defined, $X_1$ is oxygen or sulfur, Z is bromine or iodine, and M is an alkali metal.

The foregoing procedure utilizes a bromo or iodo substituted-2-amino pyridine (VII) and an alkali metal salt of an appropriately substituted phenol or thiophenol (VIII). The starting materials are combined in a solvent such as a loweralkanol, dimethyl acetamide, N-methyl pyrrolidinone, and the like. The reaction is optionally assisted by a catalyst such as powdered copper or cuprous chloride. The mixture is sealed and heated at from 100° to 250° C for from 2 to 48 hours. The product is isolated from the reaction mixture by techniques known to those skilled in the art. The pyridyl ether or thioether, thus, isolated is then cyclized according to the above described cyclization procedures.

In addition, certain of the above produced aminopyridines (II) can be converted to other compounds either prior to or subsequent to cyclization. Whether a certain group is reacted to form another group prior to or subsequent to cyclization is determined by such factors as convenience, reactivity of starting materials, side reactions, availability and necessity of protecting groups and the like. Very often a particular reaction to form a particular $R_1$ or $R_3$ group may equally well be conducted before or after cyclization. For example, the sulfide compounds can be selectively oxidized to the sulfinyl compounds or to the sulfones using oxidation techniques. The oxidation reagents used for producing the sulfoxides should be mild reagents such as -m-chlorobenzoic acid and peracetic acid. Stronger oxidation reagents may be employed for producing the sulfones. Exemplary are trifluoroperacetic acid, hydrogen peroxide and the like.

An alternative preparation of the aryl ether of 2-aminopyridine consists of a metal salt of 5-hydroxy-2-methyl pyridine with the appropriate aryl halide in a high boiling polar solvent such as dimethyl formamide or pyridine or even excess aryl halide as solvent. It is helpful to add a small amount of a catalyst such as cuprous bromide. The product, a 5-aryloxy-2-methyl pyridine, is isolated using techniques known to those skilled in the art.

Subsequently the methyl group could be oxidized to a carboxy group with strong oxidizing agents such as selenium dioxide or potassium permanganate. The reaction is generally run in aqueous media at from 50° C to the reflux temperature of the reaction mixture. The carboxylic acid is then converted to the acid halide, preferably the acid chloride with, for example, a thionyl halide, preferably thionyl chloride. The acid halide is then converted to the corresponding azide with alkali metal azide such as sodium azide. The reaction is run at from 0° to 10° C and the azide isolated with known techniques. The azide is solvolitically rearranged, preferably in aqueous acidic media, such as aqueous acetic acid. The resultant 5-phenoxy-2-amino pyridine is isolated and employed to prepare the corresponding imidazo [1,2-a] pyridine.

In addition, certain of the R groups may be converted into other R groups. Such processes may be conducted early in the synthesis in order to prepare the various starting materials (compound II) or such interconversions may be carried out upon the final product. The determination as to when such a reaction should be carried out is, as aforementioned, dependent upon many factors such as convenience, reactivity of starting materials, side reaction, availability and necessity of protecting groups and the like.

For example, a nitro group on the phenyl ring may be reduced using catalytic or chemical reduction to the amino group. Catalysts such as active metals, particularly palladium, on an inert substrate such as carbon, in an atmosphere of hydrogen is an efficient method for the preparation of the amino group. The reaction is usually conducted at room temperature and is complete when the reaction mixture no longer absorbs hydrogen gas.

An unsubstituted phenoxy or phenylthio group of compounds I or II may be chlorosulfonated with chlorosulfonic acid. The reaction is generally conducted at depressed temperatures preferably from −20° to 10° C, optionally with a solvent, however, it is generally preferred not to use a solvent. The reaction is complete in from about 2 to 48 hours and the chlorosulfonic acid is isolated using techniques known in the art.

The chlorosulfonic acid may then be treated with water and a base such as alkali metal bicarbonate to prepare the sulfonic acid (sulfo) group. The reaction is conducted at from room temperature to 100° C and is complete in from 1 to 24 hours.

Also the chlorosulfonic acid compound can be treated with ammonia or a mono- or di-loweralkylamine to prepare the sulfonamide or the N-loweralkyl or N,N-diloweralkyl derivative thereof. The reaction is generally conducted at from 0° to 100° C in optional solvent such as a loweralkanone or water. The amine is employed in excess in order to neutralize the mole of hydrochloric acid liberated during the course of the reaction. Optionally a basic solvent such as pyridine or triethylamine is employed for such purposes. The reaction is complete in from 1 to 24 hours and the product isolated by known techniques.

The loweralkoxycarbonyl group is readily converted to the carboxy group by hydrolysis. Acid catalysis is preferred using dilute hydrohalic, preferably hydrochloric, or other mineral acids, at a temperature of from 50° to 100° C. The reaction is complete in from 1 to 24 hours and the product isolated by known techniques.

The aminophenyl group is readily converted to a loweralkanoyloxy group through a diazonium salt and a fluoroborate salt. The diazonium salt is prepared in acidic media such as a mineral acid, preferably hydrochloric acid, using an alkali metal nitrate, preferably sodium nitrite. The diazonium salt is prepared at from −20° to 10° C. The diazonium salt is converted to the fluoroborate salt with hydrofluoroboric acid at from −20° to 10° C. The fluoroborate salt is isolated and treated with a lower alkanoic acid at from 50° C to the reflux temperature of the reaction mixture for a period of from ½ to 6 hours. The product is isolated using standard techniques.

In addition, the above-described fluoroborate salt may be treated with an alkali metal or alkaline earth metal cyanide to prepare the cyano compound. The reaction is run in a suitable solvent, preferably dimethylsulfoxide, and is complete in from 10 minutes to 4 hours at from 0° C to room temperature. An exotherm may be observed as the starting materials are initially combined, however, this may be readily moderated with external cooling.

Subsequently the loweralkanoyloxy group may be hydrolized to the hydroxy group using techniques such as base catalyzed hydrolysis. Bases such as alkali metal hydroxides, carbonates or bicarbonates are suitable but alkali metal hydroxides such as sodium hydroxide or potassium hydroxide are preferred.

The compounds of this invention wherein the amido group is in the 3-position of the imidazo [1,2-a] pyridine molecules are prepared by acylating an appropriately substituted 3-amino compound according to the following reaction scheme:

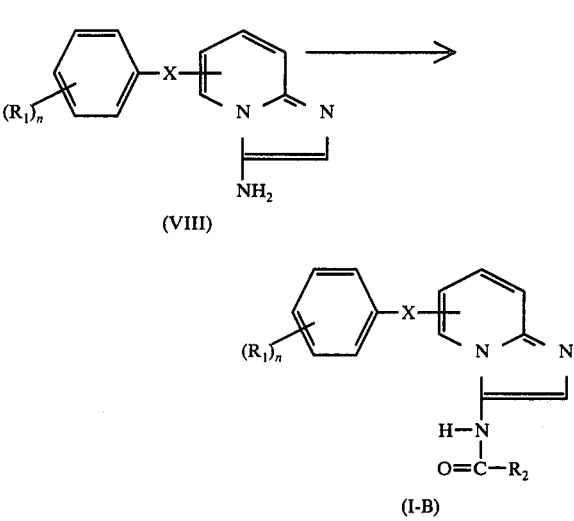

wherein X, R₁, R₂ and n are as previously defined. The foregoing acylation is carried out with acylating agents such as acyl halide, anhydrides, alkylhaloformates and the like. The procedures employed are the same as those described for the preparation of compound I-A from VI and the products (I-B) are isolated using techniques known to those skilled in this art. The R₃ substituted compounds may be prepared from products I-B via the metal salts intermediates using the procedure discussed above.

The starting materials for the foregoing process (VIII) are prepared from a halogenated-2-amino pyridine according to the following reaction scheme:

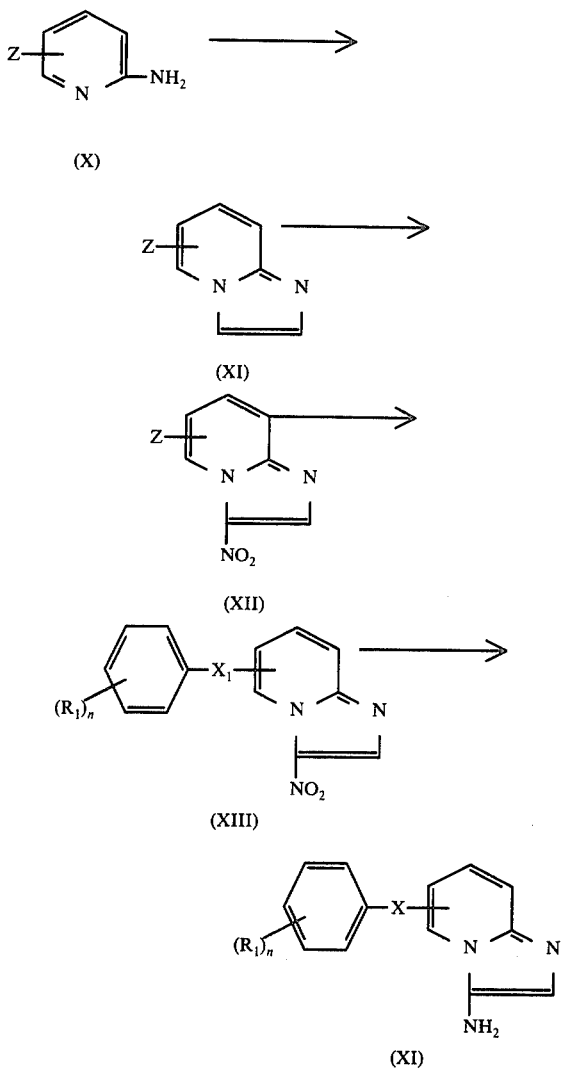

wherein $R_1$, $X_1$, $Z$ and $n$ are as previously defined.

In the first step of this process a 2-aminoiodo or bromo pyridine (X) is reacted with a halo acetaldehyde preferably chloroacetaldehyde or bromoacetaldehyde. Generally the haloacetaldehydes are only available as the acetals thereof, in which case, prior to reactions with the 2-amino pyridine compound, it is treated with acid to hydrolize the acetals, leaving the free haloacetaldehyde. A buffer may be added as needed to regulate the pH. The hydrolysis is generally carried out at from 50° C to the reflux temperature and is complete in generally less than one hour. The free haloacetaldehyde is used as soon as possible in the reaction with the 2-amino halo pyridine. The reaction carried out at from 50° C to reflux temperatures generally in a mixture of an organic solvent and water such as a loweralkanol and water. The reaction is generally complete in from 5 minutes to 2 hours and the product bromo or iodo imidazo [1,2-a] pyridine (XI) is isolated using known techniques.

Compound (XI) is then nitrated using standard nitration techniques to prepare compound (XII), the 3-nitro imidazo [1,2-a] pyridine. Preferably a mixture of concentrated nitric and sulfuric acids is employed and the reaction is run at from 0° to 50° C for from 10 minutes to 2 hours. It is generally advisable to maintain the temperature at from 0° to 20° C during the initial period of the reaction, and when the addition is complete to raise the temperature to from 20° to 50° C. The product (XII) is isolated using standard techniques.

The nitrated compound is then reacted with an appropriately substituted metal salt of phenol or thiophenol following the same procedures employed to convert compounds (VII) and (VIII) to compound (II).

Compound (VIII) is then reduced, preferably by catalytic reduction under hydrogen, to the amino compound (IX). The reduction is carried out, preferably at about room temperature, until hydrogen uptake is complete, and the product isolated using techniques known to those skilled in this art.

The best mode contemplated by Applicants for carrying out their invention is set forth in the following examples; it being understood that these examples are for purposes of illustration merely and no limitation is intended except as set forth in the appended claims.

EXAMPLE 1

2-Amino 5-iodo pyridine

150 G. of 2-amino pyridine in 600 ml. of water is treated with 420 g. of iodine and 420 g. of potassium iodide in 2400 ml. of water. The reaction mixture is stirred at room temperature overnight. The aqueous layer is decanted and the reside combined with 3600 ml. of 3% potassium hydroxide and heated on a steam bath for 10 minutes. The supernatant liquid is decanted and the residue extracted with ether and the ether extracts washed with aqueous sodium thiosulfate and water. The ether layer is dried and evaporated to dryness in vacuo affording 120 g. of 2-amino 5-iodo pyridine, m.p. 118° to 120° C.

EXAMPLE 2

2-Amino 5-phenylthio pyridine

A. 11 G. (0.05 moles) of 2-amino 5-iodo pyridine, 7.2 ml. (0.07 moles) of thiophenol, 3.8 g. (0.07 moles) of sodium methoxide, 1.0 g. of copper powder and 100 ml. of methanol are heated 150° C for 12 hours in a glass lined bomb. The reaction mixture is concentrated to dryness, extracted with chloroform and the chloroform extracts concentrated to dryness in vacuo affording 15 g. of a crude product which is chromatographed on 600 g. of silica gel, eluting with methylene chloride and ethyl acetate-methylene chloride 50 % mixture affording 6.5 g. of 2-amino 5-phenylthio pyridine, m.p. 127 to 129° C.

B. A suspension of 12 g. (0.081 moles) of potassium phenyl thiolate and 10 g. (0.058 moles) of 2-amino 5-bromopyridine in 50 ml. of 1-methyl-2-pyrollididone is heated at reflux for 4 ½ hours under a nitrogen atmosphere. The cooled reaction mixture is then poured onto 500 ml. of an ice-water mixture. The resultant precipitate is collected by filtration and washed with water. After drying, the precipitate is recrystallized from chloroform-hexane mixture to yield 5.8 g. of amino-5-phenylthiopyridine.

EXAMPLE 3

2-(Methoxycarbonylamino)-6(phenylthio) imidazo [1,2-a] pyridine

A. 6-Phenylthio 2-p-toluenesulformamidopyridine

A suspension of 92.4 g. (0.457 mole) of 2-amino 5-phenylthiopyridine and 79.3 g. (0.416 mole) of p-toluenesulfonylchloride in 600 ml. of pyridine are heated at steam bath temperature for 1 hour. After the cooled reaction mixture is diluted with 3000 ml. ice water, the resultant solid is collected and the product (m.p. 120°–127° C) is washed with water and dried at 60° C in vacuo. Recrystallization from ethanol yields pure 6-phenylthio-2-p-toluene-sulfonamido pyridine m.p. 128°–130° C.

B. 1-Carbamyl methyl) 6-(phenylthio)-2-(p-toluene sulfonamido)-pyridine

A solution of 6.45 g. (0.018 moles) of 6-phenylthio-2-p-toluenesulfonamidopyridine in 30 ml. of dimethyl formamide is treated portionwise with 0.812 g. (0.02 moles) of 57% sodium hydride dispersion. After the addition is complete, the reaction mixture is warmed to 100° C for 5 minutes. The suspension is cooled and 1.87 g. (0.020 moles) of chloroacetamide is added. The reaction mixture is heated for 2 hours at 100° C. After cooling, the reaction mixture is poured onto 300 ml. of ice water. The product is collected by filtration, washed well with water and dried in vacuo. Recrystallization of ethanol yields 4.7 g. of pure 1-carbamylmethyl 6-phenylthio-2-p-toluene sulfonamidopyridine, m.p. 164°–165° C.

C. 6-(Phenylthio)-2-(trifluoroacetamido) imidazo [1,2-a] pyridine 0.500 G. of 1-carbamylmethyl 6-phenylthio-2p-toluenesulfonamido pyridine is suspended in 10 ml. of trifluoroacetic anhydride and heated at reflux for 90 minutes. After evaporation, the residue is treated with aqueous sodium bicarbonate and the suspension is extracted with 3 portions of methylene chloride. Evaporation of the solvent in vacuo yields 6-(phenylthio)2-(trifluoroacetamido) imidazo [1,2-a] pyridine.

D. 2-Acetamido-6-(phenylthio) imidazo [1,2-a] pyridine

30 G. of 1-carbamylethyl 6-phenylthio-2-p-toluenesulfonimido pyridine is heated at reflux with 10 ml. of acetic anhydride. After evaporation of the excess acetic anhydride, the residue is dissolved in 10 ml. of ethanol and diluted with 2.5 N sodium hydroxide. The resultant precipitate is collected by filtration and washed with water. Recrystallization from ethanol yields pure 2-acetamido 6-(phenylthio) imidazo [1,2-a] pyridine m.p. 257°–259° C.

E. 2-Amino 6-(phenylthio) imidazo [1,2-a] pyridine

A suspension of 0.200 g. of 6-(phenylthio) 2-(trifluoroacetamido) imidazo [1,2-a] pyridine in 1 ml. of 2.5 N aqueous sodium hydroxide is stirred for 90 minutes at room temperature. The reaction mixture is extracted with methylene chloride and the extracts are washed with water and dried over magnesium sulfate. Evaporation of the solvent yields 2-amino 6-(phenylthio) imidazo [1,2-a] pyridine, m.p. 110°–112° C.

Hydrolysis of the 2- acetamido derivative obtained in part D of this Example is accomplished by heating 300 mg. of the 2-acetamido derivative with 12 ml. of 30% aqueous sodium hydroxide at 130° C for 2 hours. The reaction mixture, after workup as above yields the desired amine.

F. 2-(Methoxycarbonylamino 6-(phenylthio) imidazo [1,2-a] pyridine 0.200 G. of 2-amino 6-(phenylthio) imidazo [1,2-a] pyridine is suspended in 2.2 ml. of water and treated dropwise with 0.0140 gm. of methyl chloroformate. After stirring the reaction mixture for 30 minutes at room temperature, solid sodium bicarbonate (0.111 gm.) is added in small portions. The solids are collected by filtration washed with water and dried. After recrystallization from ethanol, the purified 2-methoxycarbonylamino-6-(phenylthio) imidazo 1,2-a] pyridine m.p. 247°–249° C is obtained.

EXAMPLE 4

2-(Methoxycarbonylamino) 6-(phenylthio) imidazo [1,2-a] pyridine

A. Methylchloroacetylcarbamate

A suspension of 122.6 g. of 2-chloroacetamide in 300 ml. of dichloroethane is cooled to 0° C. One portion (200 g.) of oxalylchloride is added thereto. The reaction mixture is allowed to come to room temperature and refluxed for 4 hours. The reaction mixture is cooled to 5° to 10° C and 68 ml. of methanol is added dropwise. The reaction is exothermic and external cooling id required to maintain the temperature below 15° C. The addition requires 45 minutes. When the addition is complete, the reaction mixture is stirred for 10 minutes and filtered. The solid material is washed once with dichloroethane and 3 times with ether and dried affording 129.2 g. of methylchloroacetylcarbamate m.p. 132°–134° C. Recrystallization from methylene dichloride yields pure product m.p. 142°–144° C.

B. 2-(Methoxycarbonylamino)-6-(phenylthio) imidazo [1,2-a] pyridine 2.0 G. of 2 amino-6-phenylthiopyridine, as prepared in Example 2 and 2.59 g. of methylchloroacetyl carbamate in 10 ml. of hexamethylphosphoramide is heated at 100° C for 5 hours. After cooling, the reaction mixture is diluted with water. The solids are collected by filtration washed with water, ethanol and finally methylene chloride to yield 1.3 g. of 2-(methoxycarbonylamino) 6-(phenylthio) imidazo [1,2-a] pyridine, m.p. 244°–246° C.

Alternatively one may treat 116.5 g. (0.577 moles) of 2-amino 5-phenylthio pyridine 92.9 g. (0.615 moles) of the methylchloroacetyl carbamate and 1572 ml. of dimethoxy ethane at reflux for 92 hours. The reaction mixture is cooled, diluted with an equal volume of ether and the solid material separated by filtration. The solid material is washed twice with ether, suspended in 800 ml. of saturated sodium bicarbonate, and stirred for one half hour. The suspension is filtered and the solid material washed twice with water and dried. The dry cake is washed with 1 liter of methylene chloride and dried at 50° C in vacuo affording 43.5 g. of 2-(methoxycarbonylamino) 6-(phenylthio) imidazo [1,2-a] pyridine m.p. 246°–248° C.

EXAMPLE 5

5-(p-acetamidophenylthio)2-amino pyridine 5.5 G. (0.25 mole) of 2-amino-5-iodopyridine, 5.02 g. (0.030 mole) of 4-acetamidothiophenol and 1.6 g. of sodium methoxide 800 mg. of copper under the conditions as in Example 2 (A) one obtains 5.8 g. of 5(p-acetamidophenyl) 5-(p-acetamidophenylthio)2-amino pyridine m.p. 178°–179° C.

Additional 2-aminopyridine compounds are prepared following the foregoing procedures. The following table lists the R group, the weight of the reactants and the product m.p. according to the following reaction:

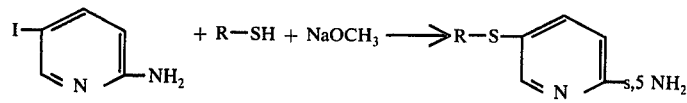
| R | (A) Weight of A | (B) Weight of B | (C) Weight of C | (D) Weight of D |
|---|---|---|---|---|
| 4-CH₃-C₆H₄- | 22 g. | 14.8 g. | 6.48 g. | 141–143° C |
| 4-N(CH₃)₂-C₆H₄- | 5.5 g. | 4.59 g. | 1.62 g. | 150–151° C |
| 4-OCH₃-C₆H₄- | 11.0 g. | 9.8 g. | 3.78 g. | 107–111° C |
| 4-Cl-C₆H₄- | 11.0 g. | 9.8 g. | 2.90 g. | |
| 2,5-Cl₂-C₆H₃- | 11.0 g. | 9.8 g. | 2.97 g. | 89–95° C |
| 2-CH₃-C₆H₄- | 11.0 g. | 9.8 g. | 3.78 g. | |
| 3-OCH₃-C₆H₄- | 11.0 g. | 9.8 g. | 3.78 g. | 106–112° C |
| 4-NO₂-C₆H₄- | 11.0 g. | 8.5 g. | 2.97 g. | 90–119° C |
| 4-SCH₃-C₆H₄- | 5.0 g. | 5.0 g. | 1.7 g. | 124–128° C |

-continued

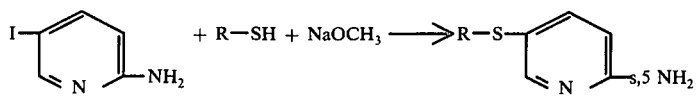

| R | (A) Weight of A | (B) Weight of B | (C) Weight of C | (D) Weight of D |
|---|---|---|---|---|
| 3-(NHC(O)CH₃)-phenyl | 5.50 g. | 5.02 g. | 1.62 g. | 139–141° C |
| 4-(CH₃SO₂)-phenyl | 5.0 g. | 6.0 g. | 1.7 gms. | 150–151° C |
| 4-(CH₃S(O))-phenyl | 5.0 gm. | 5.48 gm. | 1.7 gms. | Amorphous |

EXAMPLE 6

The 2-amino pyridine compounds of Example 5 are cyclized using methylchloroacetylcarbamate in hexamethylphosphoramide, following the procedure of Example 4B. The following table lists the weight of the reactants and the product m.p. according to the following reaction:

R—S—(pyridine)—NH₂ (D) + ClCH₂—C(O)—NH—C(O)—OCH₃ (E) → R—S—(fused bicyclic)—N—C(O)—OCH₃ (F)

| R | Weight D | Weight E | M.P.F. |
|---|---|---|---|
| 4-CH₃-phenyl | 2.16 g. | 1.8 g. | 232 – 234° C |
| 4-N(CH₃)₂-phenyl | 0.245 g. | 0.197 g. | 246 – 248° C |
| 4-OCH₃-phenyl | 2.3 g. | 1.8 g. | 228 – 230° C |
| 4-Cl-phenyl | 1.18 g. | 1.8 g. | 232 – 234° C |
| 2,4-diCl-phenyl | 2.7 g. | 1.8 g. | 240° C (dec.) |
| 2-CH₃-phenyl | 2.16 g. | 1.8 g. | 230 – 232° C |
| 3-OCH₃-phenyl | 2.3 g. | 1.8 g. | 212 – 213° C |
| 4-NO₂-phenyl | 2.47 g. | 1.8 g. | 275 – 277° C |
| 4-(SCH₃)-phenyl | 1.0 g. | 0.727 g. | 222° C (dec.) |

-continued

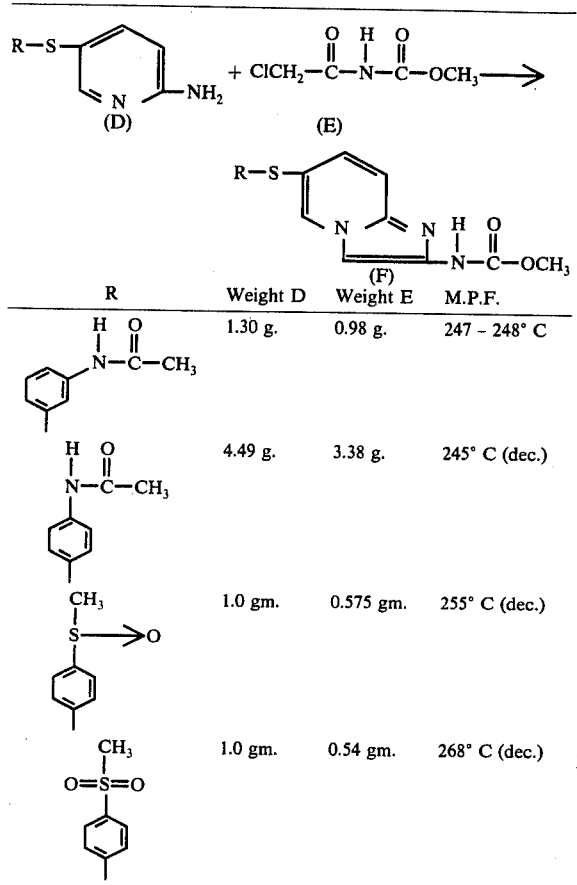

| R | Weight D | Weight E | M.P.F. |
|---|---|---|---|
| 3-(NHCOCH₃)-phenyl | 1.30 g. | 0.98 g. | 247 – 248° C |
| 4-(NHCOCH₃)-phenyl | 4.49 g. | 3.38 g. | 245° C (dec.) |
| 4-(S(CH₃)=O)-phenyl | 1.0 gm. | 0.575 gm. | 255° C (dec.) |
| 4-(SO₂CH₃)-phenyl | 1.0 gm. | 0.54 gm. | 268° C (dec.) |

EXAMPLE 7

2-(Methoxycarbonylamino) 6-(p-aminophenylthio) imidazo [1,2-a] pyridine

A suspension of 0.130 gms. of 2-(methoxycarbonylamino) 6-(p-nitrophenylthio) imidazo [1,2-a] pyridine in 30 ml. of glacial acetic acid is reduced at 40 psi. of hydrogen with 0.130 gm. of 5% palladium on carbon. When the uptake of hydrogen is complete, the catalyst is removed by filtration and the filtrate is evaporated to dryness in vacuo. The residue is stirred with saturated qqueous sodium bicarbonate and the resultant solids are collected by filtration, washed with water and dried in vacuo. The product melts 120°–175° C. Mass spectral data confirms the molecular ion of the product.

EXAMPLE 8

2-(Methoxycarbonylamino) 6-(p-sulfophenylthio) imidazo [1,2-a] pyridine

A. 2-(Methoxycarbonylamino) 6-(p-chlorosulfonylphenylthio) imidazo [1,2-a] pyridine 4.5 gms. (0.015 mole) of 2-methoxycarbonylamino 6-(phenylthio) imidazo [1,2-a] pyridine is added portionwise to 45 ml. of chlorosulfonic acid at 0° to −5° C. The reaction mixture is stirred at room temperature for 24 hours. The solution is poured onto ice and the solids are collected by filtration. After repeated washes with water, the crude chlorosulfonic acid derivative is dried at room temperature in vacuo.

B. 2-(Methoxycarbonylamino) 6-(p-sulfophenylthio) imidazo [1,2-a] pyridine 2.0 Gm. of the crude sulfonylchloride obtained above is suspended in 20 ml. of water containing 1.0 g. of sodium bicarbonate. After heating on the steam bath for 5 hours, the reaction mixture is cooled and the solids are collected by filtration. The solid cake is washed with water and dried in vacuo at 70° C to yield the sodium salt of 2-(methoxycarbonylamino) 6-(p-sulfophenylthio) imidazo [1,2-a] pyridine. Trituration of the sodium salt with 5% aqueous hydrochloric acid yields the free sulfonic acid.

EXAMPLE 9

2-(Methoxycarbonylamino) 6-[p-(N,N-dimethylsulfonamido)-phenylthio] imidazo [1,2-a] pyridine The crude sulfonylchloride (1.0 gm.) obtained in Example 7A is dissolved in acetone and added to 15 ml. of acetone containing 4 ml. of 0.40% aqueous dimethylamine. The reaction mixture is stirred overnight at room temperature, diluted with 5 volumes of water and filtered. The cake is washed with water and dried in vacuo. Recrystallization from ethanol diemthylformamide yields pure 2(methoxycarbonylamino) 6-[p(N,N-dimethylsulfonamido)phenylthio] imidazo [1,2-a] pyridine.

EXAMPLE 10

2(Methloxycarbonylamino) 6-(p-sulfonamidophenylthio) imidazo [1,2-a] pyridine

Reaction of the crude sulfonyl chloride obtained in Example 7A with 50 ml. of concentrated ammonium hydroxide on the steam bath yields 2-(methoxycarbonylamino) 6-p-(sulfonamidophenylthio) imidazo [1,2-a] pyridine.

EXAMPLE 11

2-(Methoxycarbonylamino) 6-(m-trifluoromethylphenylthio) imidazo [1,2-a] pyridine A. 2-Amino -5-(m-trifluoromethylphenylthio) pyridine Reaction of 10.68 gm. of m-trifluoromethylthiophenol, 11.0 g. of 2-amino 5-iodopyridine, 3.24 g. of sodium methoxide and 1.6 g. of copper under the conditions as in Examle 2A, affords 2-amino 5-(m-trifluoromethylphenylthio) pyridine.

B. Cyclization of the above substituted pyridine using methylchloroacetylcarbamate in hexamethylphosphoroamide as in Example 4B yields 2(methoxycarbonylamino) 6-(m-trifluoromethylphenylthio) imidazo [1,2-a] pyridine.

EXAMPLE 12

Other 2-amino pyridines are prepared following the same procedures employing the following reagents:

| A. 2-AMino 5-(p-carbomethoxyphenylthio) pyridine | |
|---|---|
| From p-carbomethoxybenzenethiol | 10.09 g. |
| 5-iodo 2-amino pyridine | 11.0 g. |
| sodium methoxide | 3.24 gm. |
| copper | 1.6 gm. |

| B. 5-(Acetylphenylthio) 2-amino pyridine | |
|---|---|
| From 4-mercapto acetophenone | 9.13 gm. |
| 5-iodo 2-amino pyridine | 11.0 gm. |
| sodium methoxide | 3.24 gm. |
| copper | 1.6 gm. |

| C. 5-(p-acetamidophenylthio) 2-amino pyridine | |
|---|---|
| From 4-mercapto benzamide | 7.27 g. |
| 5-iodo 2-amino pyridine | 11.0 gm. |
| sodium methoxide | 3.24 gm. |
| copper | 1.6 gm. |

| D. 2-Amino 5-(dimethylcarboxamidephenylthio) pyridine | |
|---|---|
| From N,N-dimethyl 4-mercaptobenzamide | 10.87 gm. |
| 5-iodo 2-aminopyridine | 11.0 gm. |
| sodium methoxide | 3.24 gm. |
| copper | 1.6 gm. |

| E. 2-Amino 5-(4-methoxycarbonylaminophenylthio) pyridine | |
|---|---|
| From 4-methoxycarbonylaminophenylthiol | 10.15 gm. |
| 5-iodo 2-aminopyridine | 11.0 gm. |
| sodium methoxide | 3.24 gm. |
| copper | 1.6 gm. |

EXAMPLE 13

Cyclization to imidazo [1,2-a] pyridine

A. The reaction of 10.4 gm. of the product of Example 12A with 6.08 gms. of methylchloroacetylcarbamate is hexamethyl phosphoramide as in Example 4B yields 2-(methoxycarbonylamino) 6-(p-carbomethoxyphenylthioimidazo [1,2-a] pyridine.

B. The reaction of 9.77 gm. of the product of Example 12B with 6.08 gms. of methylchloroacetylcarbamate in hexamethylphosphoramide as in Example 4B yields 2-(methoxycarbonylamino) 6-(acetylphenylthio) imidazo [1,2-a] pyridine C. The reaction of 8.52 gms. of the product of Example 12C with 6.08 gm. of methylchloroacetylcarbamate in hexamethylphosphoramate as in Example 4B yields 2-(methoxycarbonylamino) 5-(p-carboxamidephenylthio) imidazo [1,2-a] pyridine.

D. The reaction of 10.9 gms. of the product of Example 12D with 6.08 gm. methylchloroacetylcarbamate in hexamethyl phosphoramide as in Example 4B yields 2-(methoxycarbonylamino) 6-(p-dimethylcarboxamidophenylthio) imidazo [1,2-a] pyridine.

E. The reaction of 6.45 gms. of the product of Example 12E with 6.08 gms. methylchloroacetylcarbamate in hexamethyl phosphoramide as in Example 4B yields 2-(methoxycarbonylamino) 6-(p-methoxycarbonylaminophenylthio) imidazo [1,2-a] pyridine.

EXAMPLE 14

2-(Methoxycarbonylamino) 6-(p-carboxyphenylthio) imidazo [1,2-a] pyridine 1.0 Gm. of the product of Example 13A is suspended in 20 ml. of 10% aqueous hydrochloric acid is heated on the steam bath for 5 hours. The reaction mixture is cooled and adjusted to ph 5 with aqueous sodium bicarbonate. The solids are collected by filtration, washed with water and dried in vacuo to yield 2-(methoxycarbonylamino-6-p-carboxyphenylthio) imidazo [1,2-a] pyridine.

EXAMPLE 15

2(Methoxycarbonylamino) 6-(p-acetoxyphenylthio) imidazo [1,2-a] pyridine

A solution of 2.0 gms. of 2-(methoxycarbonylamino) 6-(p-aminophenylthio) imidazo [1,2-a] pyridine in 10 ml. of concentrated hydrochloric acid is cooled to 0° C. Dropwise a solution of sodium nitrite 0.481gm. is added while maintaining a temperature of 0° to 5° C. After addition is complete, the reaction mixture is stirred at 5° C. for 30 minutes and 20 ml. of 40% hydrofluoroboric acid is added. The resultant fluoroborate salt is collected by filtration, washed with water and dried in vacuo at room temperature. 2.0 G. of the fluoroborate salt is refluxed in 10 ml. of glacial acetic acid. After the evolution of nitrogen ceases, the reaction mixture is dilated with an equal volume of water and the solids collected by filtration. The cake is washed with water and dried in vacuo to yield 2-(methoxycarbonylamino) 6-(p-acetoxyphenylthio) imidazo [1,2-a] pyridine.

EXAMPLE 16

2-(Methoxycarbonylamino) 6-(p-hydroxyphenylthio) imidazo [1,2-a] pyridine 1.0 Gm. of the acetate derivative obtained in Example 15 is heated with a 10 ml. 50% methanol-water solution of .5 g. of potassium hydroxide for one hour. After evaporation of the methanol in vacuo the reaction mixture is acidified with glacial acetic acid. The resultant solids are removed by filtration, washed with water and dried to yield 2-(methoxycarbonylamino) 6-(p-hydroxyphenylthio) imidazo [1,2-a] pyridine.

EXAMPLE 17

2-Methoxycarbonylamino 6-(p-cyanophenylthio) imidazo [1,2-a] pyridine

A solution of 3.7 g. of cuprous cyanide and 2.6 g. of finely powdered sodium cyanide in 20 ml. of dimethyl sulfoxide is treated dropwise with a solution of 4.12 g. (.01 mole) of the diazonium tetrafluoroborate salt of 6-(aminophenylthio)-2-(methoxycarbonylamino) imidazo [1,2-a] pyridine obtained in Example 15 in 10 ml. of dimethyl sulfinate. An exotherm is observed and external cooling is necessary. The reaction mixture is stirred at room temperature for 1 hour, diluted with water and the solids collected by filtration. The solids are washed with water, dried and recrystallized from dimethylformamide-ethanol (50/50) to yield 6-(p-cyanophenylthio)-2-(methoxycarbonylamino) imidazo [1,2-a] pyridine.

EXAMPLE 18

2-(Methoxycarbonylamino) 6-(phenylsulfinyl) imidazo [1,2-a] pyridine

20 G. of the product of the Example 3 is suspended in 400 ml. of acetic acid treated with 80 ml. of 30% hydrogen peroxide and stirred at room temperature for 4 hours. The reaction mixture is filtered and the filtrate combined with 1200 ml. of water and stirred at room temperature for 15 minutes. The mixture is filtered and the solid material washed 4 times with water and dried. The solid material is dissolved in 350 ml. of dimethylformamide at 80° C. filtered and the filtrate is diluted with 350 ml. of ethanol. Upon cooling, the solids are collected by filtration and washed 3 times with ether affording 5.7 g. of 2-(methoxycarbonylamino) 6-(phenylsulfinyl) imidazo [1,2-a] pyridine m.p. 249°–251° C.

Alternatively, 0.599 g. (0.002 mole) of the product of Example 3 is combined with 0.406 g. (0.002 moles) of metachloroperbenzoic acid (85%) in 300 ml. of methylene chloride and stirred at room temperature overnight. The solution is washed with saturated aqueous sodium bicarbonate and evaporated to dryness affording 0.75 g. of crude product which is recrystallized from methylene chloride affording 2-(methoxycarbonylamino) 6-(phenylsulfinyl) imidazo [1,2-a] pyridine m.p. 247°–248° C.

In a further modification, the foregoing procedure may be carried out on 1.01 g. (0.005 moles) of 5-phenylthio-2-amino pyridine with 1.015 g. (0.005 moles) of meta-chloroperbenzoic acid and 25 ml. of methylene chloride. The product 5-phenylsulfinyl-2-amino pyridine has a m.p. of 173°–175° C. This compound is cyclized, using the procedure of Example 4, recovering -2-(methoxycarbonylamino)-6-phenylsulfinyl-imidazo [1,2-a] pyridine m.p. 243°–246° C.

EXAMPLE 19

2-(Methoxycarbonylamino)-6-(phenylsulfonyl) imidazo [1,2-a] pyridine

Portionwise, with cooling, 0.500 g. (0.0015 mole) of 2(methoxycarbonylamino)-6-(phenylsulfinyl) imidazo [1,2-a] pyridine is added to 5 ml. of a methylene chloride solution of trifluoroperacetic acid prepared from 415 μl. trifluoroacetic anhydride and 65 μl. of 90% hydrogen peroxide. The solution is heated at reflux for 20 hours. The cooled reaction mixture is washed with 10 ml. of a saturated aqueous sodium bicarbonate solution, the organic layer is separated and chromatographed on silica gel. Elution with 50% ethyl acetate-methylene chloride yields 2-(methoxycarbonylamino) 6-(phenylsulfonyl) imidazo [1,2-a] pyridine, m.p. 300° C.

In a further modification, 5-phenylthio-2-amino pyridine may be oxidized using 1.01 g. (0.005 moles) of starting material, 2.02 g. (0.010 moles) of meta-chloroperbenzoic acid and 40 ml. of methylene chloride. The product 5-phenyl sulfonyl-2-amino pyridine is isolated with a m.p. of 201°–203° C. Following the procedure of Example 4 the sulfone is cyclized to 2-methoxycarbonylamino-6-(phenylsulfonyl) imidazo [1,2-a] pyridine which has the same infrared spectral characteristics as the product produced by the foregoing procedure.

EXAMPLE 20

2-(Methoxycarbonylamino)-7-(phenylthio) imidazo [1,2-a] pyridine

A. 4-(Phenylthio) picolinic acid hydrazide 75.3 G. of ethyl 4-chloropicolinate, and 57.2 g. of sodium phenylthiolate are heated at reflux in 1100 ml. of methanol for 5 hours. The reaction mixture is cooled, and 150 ml. of 97% hydrazine is added. The solution is heated for an additional 90 minutes. The resultant suspension is cooled, filtered and the solvent is removed in vacuo. The residue is extracted with methylenechloride and the extracts are washed in 2.5 N hydrochloric acid. After drying the methylene chloride, the extracts afford 27 gm. of crude 4-phenylthiopicolinic acid hydrazide.

B. 2-Amino 4-phenylthiopyridine

A solution of 4-phenylthiopicolinic acid hydrazide 2.3 g. (0.050 mole) in 4.3 ml. of concentrated hydrochloric acid and 25 ml. of water is cooled to 75° C and a solution of 3.55 g. of sodium nitrite in 6 ml. of water is added. The solution is stirred at 0°–5° for 20 minutes after the addition is complete. The resultant suspension is extracted with methylene chloride and the combined extracts are dried over sodium sulfate and evaporated in vacuo to yield 12.7 gm. of crude 4-phenylthio picolinic acid azide. The azide is heated in 60 ml. of 50% aqueous acetic acid at steam bath temperature for 40 minutes. The suspension is filtered and the filtrate is made basic with 50% sodium hydroxide. The solids are collected by filtration, washed with water, dried and chromatographed on silica gel. Elution with ethyl acetate yields 4-phenylthio 2-amino pyridine, the structure of which is characterized analytically.

C. 2-(Methoxycarbonylamino) 7-(phenylthio) imidazo [1,2-a] pyridine

A mixture of 2-amino 4-phenylthio pyridine, 1.0 g. (0.00494 mole) and 0.82 g. of methylchloroacetyl carbamate are heated in hexamethylphosphoramide following the procedures of Example 5 to yield 2(methoxycarbonylamino) 7-(phenylthio) imidazo [1,2-a] pyridine, m.p. 221°–223° C.

EXAMPLE 21

2-Amino-8-(phenylthio) imidazo [1,2-a] pyridine

A. 2-Amino-3-phenylthio pyridine

A mixture of 59.1 g. (0.316 mole) of 3-phenylthiopyridine, 14.7 g. (0.318 mole) of sodium amide and 84 gms. of dimethyl aniline is heated at 150°–160° C for 6 hours. After dilution with 100 ml. of water, the reaction mixture is extracted with chloroform. The combined extracts are washed with water and dried. Evaporation of the solvent in vacuo yields an oily residue. The residue is triturated with three 100 ml. portions of petroleum ether yielding 17 gm. of crude insoluble product. Proton magnetic resonance spectroscopy indicates the material is a 50/50 mixture of 2- and 6-amino derivatives. The isomers are separated on silica gel eluted with 10% ethylacetate 90% methylene chloride affording pure 2-amino 3-(phenylthio) pyridine, m.p. 108°–109° C.

B.

The reaction of 1.0 g. (0.0049 mole) of 2-amino 3-(phenylthio) pyridine, 0.82 gm. of methyl chloroacetylcarbamate in hexamethylphosphoramide as in Example 5, yields 2-(methoxycarbonylamino) 8-phenylthio imidazo [1,2-a] pyridine m.p. 169°–171° C.

EXAMPLE 22

2-(Ethoxycarbonylamino)-6(phenylthio) imidazo [1,2-a] pyridine

The reaction of 2-amino-6(phenylthio) pyridine, as prepared in Example 3D, with ethylchloroformate following the procedures of Example 3E yields 2(ethoxycarbonylamino) 6-phenylthio) imidazo pyridine, the structure of which is characterized analytically.

EXAMPLE 23

2-Amino-5-(p-nitrophenoxy) pyridine

A. Sodium salt of 2-methyl 5-hydroxy pyridine

A mixture of 19.25 g. (0.175 mole) of 2-methyl 2-hydroxy pyridine and 9.4 g. (0.175) of sodium methoxide in 500 ml. of pyridine is heated and excess methanol is azeotroped by gentle distillation of approximately 175 ml. of pyridine.

B. 2-Methyl-5-(p-nitrophenoxy) pyridine

To the solution of the sodium phenolate prepared in part A, 35.35 g. of p-nitrobromobenzene is added. The reaction mixture is heated at 110° C for 16 hours, cooled and filtered. The filtrate is evaporated to dryness in vacuo. The residue is extracted with ether and the ether extracts are washed in 100 ml. of 3 N hydrochloric acid. The aqueous layer is separated and made basic with a solution of sodium hydroxide. After extraction with ether, the washed and dried extracts yield 3.1 g. of 2-methyl-5(p-nitrophenoxy) pyridine m.p. 65°–67° C.

C. 5(p-nitrophenoxy) picolinic acid 3.0 g. of 2-methyl-5p-nitrophenoxy pyridine) is suspended in 110 ml. of water and 3.8 g. of potassium permanganate is added. The mixture is heated at 95° C and further 3.8 g. portions of potassium permanganate are added at 2 hour intervals until a total of 19 g. of permanganate is added (total heating time is 18 hours). The cooled reaction mixture is filtered, and the filtrate is concentrated in vacuo to 50 ml. volume. After extraction of the solution with ether, the ph of the aqueous layer is adjusted to ph 6 and the solution is extracted with ethyl acetate. Evaporation of the combined extracts yields 5(p-nitrophenoxy)picolinic acid, m.p. 184° C (dec.)

D. 2-Amino 5-(p-nitrophenoxy) pyridine 4.0 g. of 5(p-nitrophenoxy) picolinic acid is refluxed in 50 ml. of thionyl chloride for 1 hour. The solvents are removed in vacuo and the residue is taken up in benzene and the solvent is once again removed in vacuo. This process is repeated 3 times until all traces of thionyl chloride are removed. The crude acid chloride is dissolved in 30 ml. of acetone and cooled in an ice bath. Dropwise 1.32 g. of sodium azide in 3 ml. of water is added. The reaction mixture is stirred at 0°–5° C for 15 minutes and allowed to stand at room temperature for 15 minutes. After dilution with 120 ml. of water, the crude acylazide is removed by filtration and washed with water. The acylazide is immediately suspended in 60 ml. of 50% aqueous acetic acid and heated at 100° C for 1 hour. The cooled reaction mixture is filtered, basified to pH8 with 3N sodium hydroxide and extracted with ether, and ethyl acetate. Evaporation of the solvent in vacuo yields 2-amino 5-(p-nitrophenoxy) pyridine, m.p. 132°–135° C.

EXAMPLE 24

2-Amino-5-phenoxy pyridine 3.3 G. of potassium phenolate, 5.47 g. of 2-amino 5-iodopyridine and 1.78 g. of cuprous oxide in 150 ml. of dimethylacetamide are heated at reflux under a nitrogen atmosphere for 24 hours. The solvent is removed in vacuo and the residue is extracted with chloroform. Chromatography of the methylene chloride soluble portion with silica gel and elution with ethyl acetate yields 2-amino-5-phenoxy pyridine m.p. 67°–69° C.

EXAMPLE 25

2-(Methoxycarbonylamino)-6(p-nitrophenoxy) imidazo [1,2-a] pyridine

Reaction of 2-amino-5-(p-nitrophenoxy) pyridine with methylchloroacetyl carbamate as in Example 4, yields 2-(methoxycarbonylamino)-6-(p-nitrophenoxy) imidazo [1,2-a] pyridine m.p. 242°–243° C. (dec.)

EXAMPLE 26

2-(Methoxycarbonylamino)-6-(phenoxy) imidazo [1,2-a] pyridine

Reaction of 0.372 g. of 2-amino-5-phenoxypyridine and 0.045 g. of methylchloroacetyl carbamate as in Example 4, yields 2-(methoxycarbonylamino) 6-phenoxy imidazo [1,2-a] pyridine, m.p. 235°–237° C. (dec.)

EXAMPLE 27

3-(Methoxycarbonylamino) 6-(phenylthio) imidazo [1,2-a] pyridine

A. 6-Bromoimidazo [1,2-a] pyridine

A mixture of 75 ml. of water, 5 ml. of concentrated hydrochloric acid and 30 ml. of chloroacetaldehyde dimethyl acetal is heated at 90° for 10 minutes. After the addition of 20 g. of sodium acetate, the warm solution is poured into a solution of 25 gms. of 2-amino-5-bromopyridine in 160 ml. of 60% ethanol-water containing 10 g. of sodium acetae. The reaction mixture is refluxed for 20 minutes. The ethanol is removed in vacuo and the aqueous suspension is extracted with ethyl acetate. The combined extracts are washed with saturated aqueous sodium chloride. The organic layer is separated and extracted once with 200 ml. of 1N hydrochloric acid. The aqueous layer is separated, made basic with 2.5N sodium hydroxide and extracted with ethyl ether. Evaporation of the dried ether extracts to a small volume yields 11.6 g. of 6-bromoimidazo [1,2-a] pyridine. Further recrystallization from ethyl ether yields purified product m.p. 75°–78.5° C.

B. 3-Nitro-6-bromoimidazo [1,2-a] pyridine

A solution of 24 gms. (.122 mole) of 6-bromoimidazo [1,2-a] pyridine in 80 ml. of concentrated sulfuric acid is treated dropwise with 24 ml. of concentrated nitric acid while maintaining a temperature of 15° C. with external cooling. When the addition is complete, the reaction mixture is stirred at room temperature for ½ hour and poured onto 450 gm. of ice. The ph of the mixture is adjusted to ph 4 with aqueous potassium hydroxide and the resultant solids are collected by filtration. The filter cake is washed with water and dried. Recrystallization from methylene chloride-hexane yields pure 3-nitro 6-bromoimidazo [1,2-a] pyridine m.p. 160°–161° C.

C. 3-Nitro-6-phenylthioimidazo [1,2-a] pyridine

A solution of 1.61 g. (0.012 mole) of sodium thiophenoxide and 2.42 g. (0.01 mole) of 6-bromo-3-nitroimidazo [1,2-a] pyridine in 10 ml. N-methylpyrolidinone is heated at 150° C for 0.40 minutes under a nitrogen atmosphere. The cooled solution is poured onto 100 ml. of ice-water and the resultant suspension is extracted with ethyl acetate. The combined extracts are washed with saturated aqueous sodium chloride and dried over magnesium sulfate. Evaporation of the solvent to a small volume and dilution with N-hexane yields crystalline material. The solids are purified by chromatography on silica gel. Elution with methylene chloride yields pure 3-nitro 6-phenylthioimidazo [1,2-a] pyridine m.p. 108°-109° C.

D. 3-Amino-6-phenylthioimidazo [1,2-a] pyridine

A solution of 0.542 gm. (0.002 mole) of 3-nitro-6-phenylthioimidazo [1,2-a] pyridine in 20 ml. of dioxane is reduced at 40 psi. under a hydrogen atmosphere with 0.500 g. of 5% palladium on carbon as catalyst. When the uptake of hydrogen is complete, the catalyst is removed by filtration. The filtrate is evaporated in vacuo to yield 3-amino-6-phenylthioimidazo [1,2-a] pyridine.

E. 3-(Methoxycarbonylamino)-6-(phenylthio) imidazo [1,2-a] pyridine

A solution of 1.0 g. of 3-amino-6-(phenylthio) imidazo [1,2-a] pyridine in 25 ml. of chloroform containing 0.401 g. of triethyl amine is treated dropwise with 0.378 g. of methylchloroformate. The reaction mixture is stirred for 3 hours at room temperature. The chloroform is removed in vacuo and the residue is triturated with water. The solids are collected by filtration, washed well with water and dried. Recrystallization from dimethylformamideethane yields pure 3-(methoxycarbonylamino) 6-(phenylthio) imidazo [1,2-a] pyridine m.p. 211°-215° C.

EXAMPLE 28

3-(Methoxycarbonylamino)-6-(phenylsulfinyl) imidazo [1,2-a] pyridine

Oxidation of 3-methylcarbonylamino 6-(phenylthio) imidazo [1,2-a] pyridine using metachloroperbenzoic acid is carried out as in Example 17 affording 3-(methoxycarbonylamino)-6-(phenylsulfinyl) imidazo [1,2-a] pyridine.

EXAMPLE 29

3-(Methoxycarbonylamino)-6-(phenylsulfonyl) imidazo [1,2-a] pyridine

Following the procedure of Example 18, using the product of Example 28 as starting material, there is prepared 3-(methoxycarbonylamino)-6-(phenylsulfonyl) imidazo [1,2-a] pyridine.

EXAMPLE 30

2[Ethyl-N-(methoxycarbonyl)amino]-6-(phenylthio) imidazo [1,2-a] pyridine

A. Methyl-N-Ethyl carbamate

39 G. (0.61 moles) of 70% aqueous ethyl amine is treated dropwise with 23.6 g. of methyl chloroformate. The reaction is maintained at 25° C or below with external cooling. When the addition is complete, the reaction mixture is stirred at room temperature for 2 hours and extracted with three 500 ml. portions of ether. The combined extracts are washed with saturated aqueous sodium chloride solution and dried over magnesium sulfate. The solution is evaporated to dryness in vacuo and the residue purified by fractional distillation. The fraction distilling at 73° C/25 mm. of Hg. affords pure methyl-N-ethyl carbamate.

B. Methyl-N-Ethyl chloroacetyl carbamate

A mixture of 10.3 g. (0.01 moles) of methyl-N-ethyl carbamate and 11.3 g. (0.01 moles) of chloroacetyl chloride is heated at 130° C for 2½ hours. The reaction mixture is fractionally distilled and the fraction distilling at 92°-94° C/4mm. of Hg. affords pure methyl-N-ethyl chloroacetyl carbamate.

C. 2-[Ethyl-N-(Methoxycarbonyl)amino]-6-(Phenylthio) imidazo [1,2-a] pyridine A solution of 1.0 g. (0.005 moles) of 2-amino-5-phenylthio pyridine, 0.505 g. (0.005 moles) of methyl-N-ethyl chloroacetyl carbamate in 15 ml. of dimethoxy ethane is heated at reflux temperature for 4 hours. The solvent is then removed in vacuo and the residue triturated with chloroform. The insoluble material is removed by filtration and the filtrate eluted on a column of silica gel. The column is eluted with ethyl acetate affording 2-[ethyl-N-(methoxycarbonyl)amino]-6-(phenylthio) imidazo [1,2-a] pyridine m.p. 130°-131° C.

EXAMPLE 31

2-[Methyl-N-(Methoxycarbonyl)amino]-6-(p-phenylthio) imidazo [1,2-a] pyridine A suspension of 80 g. (0.026 moles) of 2-(methoxy carbonly-amine)-6-(phenylthio) imidazo [1,2-a] pyridine in 135 ml. of dimethyl formamide is treated portionwise with 1.24 g of 57% sodium hydride. The reaction mixture is heated on the steam bath for 30 minutes, cooled and treated dropwise with 4.17 g. (0.0294 moles) of methyl iodide. The reaction mixture is stirred overnight at room temperature and diluted with 1250 ml. of water. The resultant solid material is collected by filtration, washed with water and dried. Recrystallization from benzene affords pure 2-[methyl-N-(methoxy carbonyl)amino]-6-(phenylthio) imidazo [1,2-a] pyridine m.p. 147°-149° C.

EXAMPLE 32

Following the procedures of Examples 31 or 32, using the appropriate starting materials, the following products are obtained:

2-[allyl-N-(methoxycarbonyl)amino]-6-(phenylthio) imidazo [1,2-a] pyridine m.p. 129°-130° C.

2-(methylthiomethyl-N-(methoxycarbonyl)amino]-6-(phenylthio) imidazo [1,2-a] pyridine m.p. 138°-140° C 2-[propyl-N-(methoxycarbonyl)amino]-6-(phenylthio) imidazo [1,2-a] pyridine m.p. 115°-117° C 2-[methoxymethyl-N-(methoxycarbonyl)amino]-6-(phenylthio) imidazo [1,2-a] pyridine 2-[metoxycarbonyl)amino]-6allyl-N-(methoxycarbonyl)amino]imidazo [1,2-a] pyridine m.p. 133°-135° C 2-[methyl-N-(methoxycarbonyl)amino]-6-(phenylsulfinyl) imidazo [1,2-a] pyridine m.p. 157°-158.5° C 2-[carboxymethyl-N-(methoxycarbonyl)]-6-(phenylsulfinyl) imidazo [1,2-a] pyridine m.p. 205°-208° C 2-[methoxycarbonylmethyl-N-(methoxycarbonyl)amino]-6-(phenylsulfinyl) imidazo [1,2-a] pyridine m.p. 147° C 2-[methoxyethyl-N-(methoxycarbonyl)amino]-6-(phenylsulfinyl) imidazo [1,2-a] pyridine m.p. 102°-105° C 2-[benzyl-N-(methoxycarbonyl)amino]2-6-(phenylsulfinyl) imidazo [1,2-a] pyridine m.p. 179°-180° C 2-[p-chlorobenzyl-N-methoxycarbonyl)amino]-6(phenylsulfinyl) imidazo [1,2-a] pyridine m.p. 138°-139° C 2-[methylthioethyl-N-(methoxycarbonyl)amino]-6-(phenylsulfinyl) imidazo [1,2-a] pyridine m.p. 111°-113° C 2-[isopropyl-N-(methoxycarbonyl)amino]-6-(phenylsulfinyl) imidazo [1,2-a] pyridine (amorphous)

2-[p-methoxy benzyl-N-(methoxycarbonyl)amino]-6-(phenylsulfinyl) imidazo [1,2-a] pyridine m.p. 146°-148° C 2-[dimethylaminoethyl-N-(methoxycarbonyl)amino]-6-(phenylsulfinyl) imidazo [1,2-a] pyridine m.p. 112°-114° C 2-[dimethylamino propyl-N-(methoxycarbonyl)-]amino)-6-(phenylsulfinyl) imidazo [1,2-a] pyridine m.p. 98°-104° C 2-[ethyl-N-(methoxycarbonyl)amino]-6-(phenylsulfonyl) imidazo [1,2-a] pyridine (amorphous)

EXAMPLE 33

2-[Methylsulfinylmethyl-N-(methoxycarbonyl)amino-6-(phenylthio) imidazo [1,2-a] pyridine A solution of 100 mg. (0.00028 moles) of 2-[methylthiomethyl-N-(methoxycarbonyl)amino]-6-(phenylthio) imidazo [1,2-a] pyridine in 2 ml. of methylene chloride is treated dropwise with a solution of 56 mg. (0.00028 moles) of 85% metachloroperbenzoic acid in 7 ml. of methylene chloride. After 5 minutes, the reaction is quenched with saturated aqueous sodium bicarbonate solution. The organic layer is separated, washed with water, dried over magnesium sulfate, and evaporated to dryness in vacuo. The residue is chromatographed on silica gel, eluting with ethyl acetate affording pure 2-[methylsulfinylmethyl-N-(methoxycarbonyl)amino]-6-(phenylthio) imidazo [1,2-a] pyridine m.p. 163°-165° C.

In a manner similar to the foregoing, using the appropriate starting materials, there is obtained: 2-[ethyl-N-(methoxycarbonyl)amino]-6-(phenylsulfinyl) imidazo [1,2-a] pyridine m.p. 125°-127° C.

EXAMPLE 34

2-[Methyl-N-(methoxycarbonyl)amino]-6-(phenylthio) imidazo [1,2-a] pyridine

A suspension of 1.0 g. (0.0033 moles) of 2-(methoxycarbonylamino)-6-(phenylthio) imidazo [1,2-a] pyridine in 35 ml. of tetrahydrofuran under a argon atmosphere is treated dropwise with 1.35 ml. of a 2.45 molar solution of butyllithium in hexane at −20° C. The resultant solution is stirred for 5 minutes and 0.469 g. (0.0033 moles) of methyliodide is added. The reaction mixture is allowed to warm to room temperature and stirred for 30 minutes. The solution is diluted with ice water and the solids are collected by filtration, washed with water and dried. The solid materials is chromatographed on silica gel and eluted with 1:99 methanol in methylene chloride affording 2-[methyl-N-(methoxycarbonyl)amino]-6-(phenylthio) imidazo [1,2-a] pyridine m.p. 147°-149° C.

When the imidazo [1,2-a] pyridines of this invention are employed for the treatment and control of helminthiasis, the specific means employed for administering the imidazo [1,2-a] pyridines to the animal is not critical and any of the methods now used or available for treating animals infected with or susceptible to infection by helminths are satisfactory. Where it is desired to administer the imidazo pyridine in dry, solid unit dosage form, capsules, boluses or tablets containing the desired amount of imidazo pyridine usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of anthelmintic agent depending upon factors such as the type of host animal to be treated, the severity and type of infection and the weight of the host. For large animals such as sheep, swine and cattle, unit dosages up to 15 gm., containing from 13 to 12 gm., of imidazo pyridine, may be employed. It is usually preferred, however, to employ unit dosages weighing from 5 to 10 gm. containing from 2 to 8 gm. of imidazo pyridine. Boluses as well as smaller size tablets contain various binders and lubricants and are compounded by techniques well-known in the art. Capsules are prepared readily by mixing the active ingredient with a diluent such as starch or lactose and filling into the capsule.

In order to treat infected animals by means of a drench, the substituted imidazo pyridines of this invention are mixed with a suspending agent such as bentonite and the solid mix is added to water just prior to administration. Preferred drench formulations contain from about 5 to 50% by weight of the imidazo pyridine.

The imidazopyridine described herein also may be administered as a component of the feed of the animals or may be dissolved or suspended in the drinking water. Such compositions comprise the imidazo pyridine intimately dispersed in an inert carrier of diluent. By inert carrier, is meant one that will not react with the imidazo pyridine and one that may be administered safely to animals. Preferably, the carrier is one that is, or may be, an ingredient of the animal's ration.

Suitable compositions include feed supplements in which the active ingredient is present in relatively large amounts and which are suitable for addition to the feed either directly or after an intermediate dilution of blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active imidazo pyridines are intimately dispersed throughout the carrier by methods such as grinding, stirring, milling or tumbling. Compositions containing from about 5 to 50% by weight of the imidazo pyridines are particularly suitable as feed additives.

Examples of typical feed supplements containing the imidazo pyridines of this invention dispersed in a solid carrier are:

| | Lbs. |
|---|---|
| (A) | |
| 2-(Methoxycarbonylamino)-6(Phenylsulfinyl) imidazo ([1,2-a] pyridine | 20 |
| Corn distiller's dried grains | 80 |
| (B) | |
| 2-(Methoxycarbonylamino)-6-phenylthio-imidazo [1,2-a] pyridine | 5 |
| Wheat standard middling | 95 |
| (C) | |
| 2-(Methoxycarbonylamino)-6-(4-methoxyphenyl-thio)-imidazo 1,2-a] pyridine | 35 |
| Wheat shorts | 65 |
| (D) | |
| 2-(Methoxycarbonylamino)-6-(4-methylphenyl-thio)-imidazo [1,2-a] pyridine | 50 |
| Corn distiller's grains | 50 |

These and similar feed supplements are prepared by uniformly mixing the imidazo pyridine with the carrier.

Such supplements are added to the animal feed in an amount to give the finished feed the concentration of imidazo pyridine desired for the treatment and control of helminthiasis. Although the desired concentration of active compounds will vary depending upon the factors previously mentioned as well as upon the particular imidazo pyridine employed, the imidazo pyridine of this invention are usually fed at concentrations of between 0.5 to 2.0% in the feed in order to achieve the desired anthelmintic result.

The imidazopyridines of this invention are effective fungicides in a variety of applications. Accordingly, they may be employed as fungicides by conventional techniques in the protection of plants, soils, fruits, seeds, fur, wood, paint, textiles, cosmetics, leather, tobacco, rope, paper, pulp, plastic, fuel, rubber, food and the like.

It should be understood that the imidazo pyridine compounds may be utilized in diverse formulations, solid, including finely divided powders and granular materials as well as liquid, such as solutions, emulsions, suspensions, concentrates, emulsifiable concentrate, slurries and the like, depending upon the application intended and the formulation media desired. Thus, it will be appreciated that the imidazo pyridines of this invention may be employed to form fungicidally active compositions containing such compounds as essentially active ingredients thereof, which compositions may also include finely divided dry or liquid diluents, extenders, fillers, conditioners and excipients, including various clays, diatomaceous earth, talc and the like, or water and various organic liquids such as lower alkanols, for example ethanol and isopropanol or kerosene, benzene, toluene and other petroleum distillate fractions or mixtures thereof. The quantity of active imidazo pyridines contained in such formulations will vary widely depending upon the particular imidazo pyridines employed and the particular application intended. In general, useful formulations will contain from about 1 to about 95% of the active imidazo pyridines.

It should be understood also that the imidazo pyridines of the invention may be used in combination one with the other as well as with other fungicidally active materials. For instance, the imidazo pyridines disclosed above may be mixed with sorbic acid or its salts, propionic acid or its salts, mycostatin, sodium diacetate, trichomycin, amphotercin, griseofluvin, undecylenic acid, chloroquinadol, 5,7-dichloro-8-hydroxyquinoline (Vioform), sodium o-phenylphenate, o-phenylphenol, biphenyl, chlorinated phenols, sodium benzoate, dehydroacetic acid and its salts or esters of parahydroxybenzoic acid, such as the methyl and propyl ester (parabens) to give added fungicidal effect when used in appropriate concentrations. It is quite clear, too, that the imidazo pyridines of this invention may be used in conjunction with effective anti-bacterial materials in appropriate instances so as to combine the action of each in such a situation as to be particularly useful, for instance, in applications where the presence of bacteria creates undesirable results alongside the detrimental action of fungi. Accordingly, a combination of antifungal and anti-bacterial agents will be useful in the preparation of germicidal soaps, in the production of cosmetics, and in food, such as beer, cheese, or meat and other leather applications.

It has been found that growth of various fungi existing in soil is limited or terminated by the addition to the soil of minor quantities of the imidazo pyridine compounds described. The term soil as used herein is intended to include all media capable of supporting the growth of plants and may include humus, sand, manure, compost, artificially created plant growth solution, and the like. It has been found also that the imidazo pyridines of the invention are effective against fungal diseases of plants and may be effectively used either by direct contact with the foliage or systemically, by introduction through the roots.

The compounds of this invention also have activity against bacteria and plant nematodes and may, at appropriate levels of concentration, be effectively used to inhibit or prevent the growth of these organisms.

As fungicides, the imidazo pyridines of the present invention are useful in inhibiting mold growth in fruit such as citrus fruit. The active agent may be applied at any time before consumption and preferably after harvesting. For instance, the anti-fungal may be applied during initial storage, before or after shipping or during final storage before consumption. The imidazo pyridines may be utilized in a number of ways in this regard and may be applied either directly to the fruit in an emulsion, solution, suspension or the like or it may be applied to the fruit container or wrapper. Suitable carriers for the active agents are waxes and other materials presently known in the art.

What is claimed is:

1. A compound having the formula:

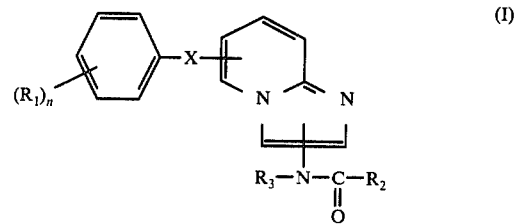

wherein
X is thio, sulfinyl or sulfonyl;
$R_1$ is halogen, trifluoromethyl, loweralkyl, loweralkoxy, loweralkoxycarbonyl, loweralkylthio, loweralkylsulfinyl, loweralkylsulfonyl, loweralkanoyl, hydroxy, sulfonamido, mono- or di-loweralkylsulfonamido, amino, mono- or di-loweralkylamino, carboxy, carboxamido, mono- and di-loweralkylcarboxamido, loweralkanoyloxy, loweralkoxycarbonylamino, loweralkanoylamino, cyano or nitro;
$n$ is 0, 1 or 2, such that when $n$ is 2, the two $R_1$ groups need not be identical;
$R_2$ is loweralkyl or loweralkoxy; and
$R_3$ is hydrogen, loweralkyl, loweralkenyl, or loweralkyl substituted with loweralkoxy, loweralkoxycarbonyl, carboxy, loweralkylthio, loweralkylsulfinyl, loweralkylsulfonyl, amino and mono- or di-loweralkylamino, phenyl, halophenyl, or loweralkoxyphenyl.

2. The compound of claim 1 in which the

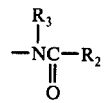

group is at the 2-positions and the phenyl containing substituent is at the 6-position of the imidazo [1,2-a] pyridine molecule.

3. The compound of claim 2 in which $R_2$ is loweralkoxy, and $R_3$ is hydrogen or loweralkyl.

4. The compound of claim 3 in which $R_2$ is methoxy or ethoxy, and $R_3$ is hydrogen, methyl or ethyl.

5. The compound of claim 2 wherein n is 0 or 1.

6. The compound of claim 5 in which n is 0, X is thio, sulfinyl or sulfonyl, and $R_2$ is loweralkoxy.

7. The compound of claim 6 which is 2-methoxycarbonylamino-6-phenylthio imidazo [1,2-a] pyridine.

8. The compound of claim 6 which is 2-methoxycarbonylamino-6-phenylsulfinyl imidazo [1,2-a] pyridine.

9. The compound of claim 6 which is 2-methoxycarbonylamino-6-phenylsulfonyl imidazo [1,2-a] pyridine.

10. The compound of claim 5 in which n is 1, $R_2$ is loweralkoxy, $R_3$ is hydrogen or loweralkyl and $R_1$ is amino, loweralkanoylamino, loweralkoxy, loweralkylsulfinyl, mono- or di-loweralkylamino, or loweralkyl, and that such groups are in the 3- or 4- position of the phenyl ring.

11. The compound of claim 10 in which $R_1$ is amino, loweralkanoylamino, or loweralkoxy in the 4-position of the phenyl ring.

12. The compound of claim 11 in which $R_2$ is methoxy, $R_3$ is hydrogen and $R_1$ is amino, acetamido or methoxy.

13. The compound of claim 12 which is 6-(4-aminophenylsulfinyl)-2-(methoxcarbonylamino) imidazo [1,2-a] pyridine.

14. The compound of claim 12 which is 6-(4-aminophenylthio)-2-(methoxycarbonylamino) imidazo [1,2-a] pyridine.

15. The compound of claim 12 which is 6-(4-acetamidophenylsulfinyl)-2-(methoxycarbonylamino) imidazo [1,2-a] pyridine.

16. The compound of claim 12 which is 6-(4-acetamidophenylthio)-2-(methoxycarbonylamino) imidazo [1,2-a] pyridine.

17. The compound of claim 12 which is 6-(4-methoxyphenylsulfinyl)-2-(methoxycarbonylamino) imidazo [1,2-a] pyridine.

18. The compound of claim 12 which is 6-(4-methoxyphenylthio)-2-(methoxycarbonylamino) imidazo [1,2-a] pyridine.

19. The compound of claim 10 which is 6-(methylsulfinylphenylthio)-2-(methoxycarbonylamino) imidazo [1,2-a] pyridine.

20. The compound of claim 10 which is 6-[4-(N-methylamino) phenylthio]-2-(methoxycarbonylamino) imidazo [1,2-a] pyridine.

21. The compound of claim 10 which is 6-[4-(N,N-dimethylamino) phenylthio]-imidazo [1,2-a] pyridine.

22. The compound of claim 10 which is 6-(4-methylphenylthio)-2-(methoxycarbonylamino) imidazo [1,2-a] pyridine.

23. The compound of claim 10 which is 2-[ethyl-N-(methoxycarbonyl)amino]-6-(phenylthio) imidazo [1,2-a] pyridine.

24. The compound of claim 10 which is 2-[ethyl-N-(methoxycarbonyl)amino]-6-(phenylsulfinyl) imidazo [1,2-a] pyridine.

25. The compound of claim 10 which is 2-[methyl-N-(methoxycarbonyl)amino]-6-(phenylthio) imidazo [1,2-a] pyridine.

26. The compound of claim 10 which is 2-[methyl-N-(methoxycarbonyl)amino]-6-(phenylsulfinyl) imidazo [1,2-a] pyridine.

27. A compound having the formula:

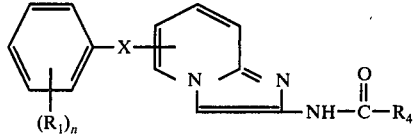

wherein
X is thio, sulfinyl or sulfonyl;
$R_1$ is halogen, trifluoromethyl, loweralkyl, loweralkoxy, loweralkoxycarbonyl, loweralkylthio, loweralkylsulfinyl, loweralkylsulfonyl, loweralkanoyl, hydroxy sulfonamido, amino, mono- or di-loweralkylamino, carboxy, carboxamido, mono- or di-loweralkylcarboxamido, loweralkanoyloxy, loweralkoxycarbonylamino, loweralkanoylamino, cyano or nitro;
$R_4$ is loweralkyl or trifluoromethyl; and
n is 0, 1 or 2 such that when n is 2 the two $R_1$ groups need not be identical.

28. An anthelmintic composition which comprises an inert carrier and a compound having the formula:

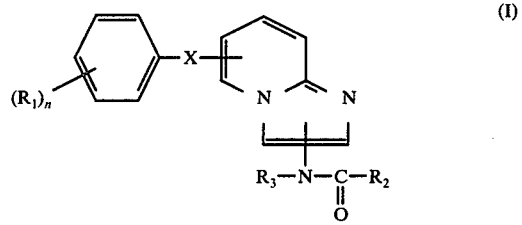

(I)

wherein
X is thio, sulfinyl or sulfonyl;
$R_1$ is halogen, trifluoromethyl, loweralkyl, loweralkoxy, loweralkoxycarbonyl, loweralkylthio, loweralkylsulfinyl, loweralkylsulfonyl, loweralkanoyl, hydroxy, sulfonamido, mono- or di-loweralkylsulfonamido, amino, mono- or di-loweralkylamino, carboxy, carboxamido, mono- and di-loweralkylcarboxamido, loweralkanoyloxy, loweralkoxycarbonylamino, loweralkanoylamino, cyano or nitro;
n is 0, 1 or 2, such that when n is 2, the two $R_1$ groups need not be identical;
$R_2$ is loweralkyl or loweralkoxy; and
$R_3$ is hydrogen, loweralkyl, loweralkenyl, or loweralkyl substituted with loweralkoxy, loweralkoxy carbonyl, carboxy, loweralkylthio, loweralkylsulfinyl, loweralkylsulfonyl, amino and mono- or di-loweralkylamino, phenyl, halophenyl, or loweralkoxyphenyl.

* * * * *